United States Patent
Knuth et al.

(10) Patent No.: US 7,125,681 B2
(45) Date of Patent: Oct. 24, 2006

(54) METHODS FOR DETECTION OF DISEASE-ASSOCIATED ANTIBODIES IN URINE

(75) Inventors: Alexander Knuth, Frankfurt am Main (DE); Elke Jäger, Frankfurt am Main (DE); Dirk Jäger, Frankfurt am Main (DE)

(73) Assignee: Ludwig Institute for Cancer Research, New York, NY (US)

( * ) Notice: Subject to any disclaimer, the term of this patent is extended or adjusted under 35 U.S.C. 154(b) by 305 days.

(21) Appl. No.: 10/176,038

(22) Filed: Jun. 21, 2002

(65) Prior Publication Data

US 2002/0197659 A1 Dec. 26, 2002

Related U.S. Application Data

(60) Provisional application No. 60/300,258, filed on Jun. 22, 2001.

(51) Int. Cl.
*G01N 33/574* (2006.01)
*C12Q 1/58* (2006.01)
*C07K 16/30* (2006.01)

(52) U.S. Cl. .............. 435/7.23; 435/7.23; 435/12; 530/387.1; 530/389.7

(58) Field of Classification Search ............. 424/140.1; 530/387.1; 435/12, 7.2, 7.23
See application file for complete search history.

(56) References Cited

U.S. PATENT DOCUMENTS 5,888,751 A * 3/1999 Tureci et al. ............. 435/7.23
6,043,084 A * 3/2000 Scanlan et al.
6,673,914 B1 * 1/2004 Hoon ..................... 536/23.5

OTHER PUBLICATIONS

Bodey (Expert Opin Biol Ther. Aug. 2002;2(6):577-84).*
Scanlan et al. (Immunological Reviews 2002; vol. 188: 22-32).*
Chen et al. (Proc. Natl. Acad. Sci. USA. 1997; vol. 94: 1914-1918).*
Murphy, G.P., Lawrence, W., and Lenhard, R.E. 1995. Clinical Oncology. 2nd edition. Atlanta, GA: American Cancer Society 470-485.*
Levine, R. 1990. Pharmacology: Drug Actions and Reactions. 4th edition. Boston, Mass: Little ,Brown & Co, 140-141.*
Merriam-Webster Online : http://www.m-w.com/cgi-bin/dictionary?book=Dictionary&va=antibody.*
Sockert et al. (J. Exp. Med. 1998; 187: 1349-1354).*
Jager (J. Exp. Med. 1998, 187:265-270).*

* cited by examiner

*Primary Examiner*—Jeffrey Siew
*Assistant Examiner*—Brandon Fetterolf
(74) *Attorney, Agent, or Firm*—Fulbright & Jaworski L.L.P.

(57) ABSTRACT

The present invention provides methods and diagnostic kits for the detection of disease-specific antibodies in urine containing sample. The present invention is also directed toward methods for determining that a patient suffers from a disorder characterized by aberrant expression of a naturally occurring gene. Methods for monitoring the status of a disorder in a patient characterized by aberrant expression of a naturally occurring gene are also provided.

4 Claims, No Drawings

SEQUENCE LISTING

<160> NUMBER OF SEQ ID NOS: 3

<210> SEQ ID NO 1
<211> LENGTH: 180
<212> TYPE: PRT
<213> ORGANISM: Homo sapien
<220> FEATURE:
<223> OTHER INFORMATION:

<400> SEQUENCE: 1

```
Met Gln Ala Glu Gly Arg Gly Thr Gly Ser Thr Gly Asp Ala
                5                   10                  15
Asp Gly Pro Gly Pro Gly Ile Pro Asp Gly Pro Gly Gly Asn
                20                  25                  30
Ala Gly Gly Pro Gly Glu Ala Gly Ala Thr Gly Gly Arg Ala Pro
                35                  40                  45
Arg Gly Ala Gly Ala Ala Arg Ala Ser Gly Pro Gly Gly Gly Ala
                50                  55                  60
Pro Arg Gly Pro His Gly Gly Ala Ala Ser Gly Leu Asn Gly Cys
                65                  70                  75
Cys Arg Cys Gly Ala Arg Gly Pro Glu Ser Arg Leu Leu Glu Phe
                80                  85                  90
Tyr Leu Ala Met Pro Phe Ala Thr Pro Met Glu Ala Glu Leu Ala
                95                  100                 105
Arg Arg Ser Leu Ala Gln Asp Ala Pro Pro Leu Pro Val Pro Gly
                110                 115                 120
Val Leu Leu Lys Glu Phe Thr Val Ser Gly Asn Ile Leu Thr Ile
                125                 130                 135
Arg Leu Thr Ala Ala Asp His Arg Gln Leu Gln Leu Ser Ile Ser
                140                 145                 150
Ser Cys Leu Gln Gln Leu Ser Leu Leu Met Trp Ile Thr Gln Cys
                155                 160                 165
Phe Leu Pro Val Phe Leu Ala Gln Pro Pro Ser Gly Gln Arg Arg
                170                 175                 180
```

<210> SEQ ID NO 2
<211> LENGTH: 3446
<212> TYPE: DNA
<213> ORGANISM: Homo sapien
<220> FEATURE:
<223> OTHER INFORMATION:

<400> SEQUENCE: 2

```
gcgcaggaac ttaagacagt tcctcctggc gatgtgatgg aatttaatgg gacaggagaa     60
gggaacgggc tttcttttca ggccagcgtg gcagcgggcg gtagggcgaa agggagaagg    120
aaacgagggt ttattccgtt gcccactccg cgatatttac aaccgtaaca gagaaaatgg    180
aaaagcaaaa gccctttgca ttgttcgtac caccgagatc aagcagcagt caggtgtctg    240
cggtgaaacc tcagaccctg ggaggcgatt ccactttctt caagagtttc aacaaatgta    300
ctgaagatga ttttgagttt ccatttgcaa agactaatct ctccaaaaat ggggaaaaca    360
ttgattcaga tcctgcttta caaaagtta atttcttgcc cgtgcttgag caggttggta    420
attctgactg tcactatcag gaaggactaa aagactctga tttggagaat tcagagggat    480
tgagcagagt gtattcaaaa ctgtataagg aggctgaaaa gataaaaaaa tggaaagtaa    540
gtacagaagc tgaactgaga cagaaagaaa gtaagttgca agaaaacaga aagataattg    600
```

```
aagcacagcg aaaagccatt caggaactgc aatgtggaaa tgaaaaagta agtttgacat      660
tagaagaagg aatacaagac aataaagatt taataaaaga gaataatgcc acaaggcatt      720
tatgtaatct actcaaagaa acctgtgcta gatctgcaga aaagacaaag aaatatgaat      780
atgaacggga agaaaccagg caagtttata tggatctaaa tagtaacatt gagaaaatga      840
taacagcttt tgaggaactt cgtgtgcaag ctgagaattc cagactggaa atgcatttta      900
agttaaagga agattatgaa aaaatccaac accttgaaca agaatacaag aaggaaataa      960
atgacaagga aaagcaggta tcactactat tgatccaaat cactgagaaa gaaaataaaa     1020
tgaaagattt aacatttctg ctagaggaat ccagagataa agttaatcaa ttagaggaaa     1080
agacaaaatt acagagtgaa aacttaaaac aatcaattga gaaacagcat catttgacta     1140
aagaactaga agatattaaa gtgtcattac aaagaagtgt gagtactcaa aaggctttag     1200
aggaagattt acagatagca acaaacacaa tttgtcagct aactgaagaa aaagacactc     1260
aaatggaaga atctaataaa gctagagctg ctcattcgtt tgtggttact gaatttgaaa     1320
ctactgtctg cagcttggaa gaattattga gaacagaaca gcaaagattg gaaaattatg     1380
aagatcaatt gataatactt accatggagc ttcaaaagac atcaagtgag ctggaagaga     1440
tgactaagct tacaaataac aaagaagtag aacttgaaga attgaaaaaa gtcttgggag     1500
aaaaggaaac actttatat gacaataaac aatttgagaa gattgctgaa gaattaaaag     1560
gaacagaaca agaactaatt ggtcttctcc aagccagaga gaaagaagta catgatttgg     1620
aatacagtta ctgccattac cacaagtgga cagtattacc caaaagaggt caaagaccaa     1680
aactgagctc gaaacgagaa ctcaagaata ctgaatactt cacactgcaa caagcttcac     1740 cccccccaa cgagctcaca caggaaacaa gtgatatgac cctagaactc aagaatcagc     1800
aagaagatat aattaataac aaaaagcaag aagaaaggat gttgacacaa atagaaaatc     1860
ttcaagaaac agaaacccaa ttaagaaatg aactagaata tgtgagagaa gagctaaaac     1920
agaaaagaga tgaagttaaa tgtaaattgg acaagagtga agaaaattgt aacaatttaa     1980
ggaaacaagt tgaaaataaa aacaagtata ttgaagaact tcagcaggag aataaggcct     2040
tgaaaaaaaa aggtacagca gaaagcaagc aactgaatgt ttatgagata aaggtcaata     2100
aattagagtt agaactagaa agtgccaaac agaaatttgg agaaatcaca gacacctatc     2160
agaaagaaat tgaggacaaa aagatatcag aagaaaatct tttggaagag gttgagaaag     2220
caaaagtaat agctgatgaa gcagtaaaat tacagaaaga aattgataag cgatgtcaac     2280
ataaaatagc tgaaatggta gcacttatgg aaaaacataa gcaccaatat gataagatca     2340
ttgaagaaag agactcagaa ttaggacttt ataagagcaa agaacaagaa cagtcatcac     2400
tgagagcatc tttggagatt gaactatcca atctcaaagc tgaacttttg tctgttaaga     2460
agcaacttga aatagaaaga gaagagaagg aaaaactcaa aagagaggca aaagaaaaca     2520
cagctactct taaagaaaaa aaagacaaga aaacacaaac attttattg gaaacacctg     2580 acatttattg gaaattggat tctaaagcag ttccttcaca aactgtatct cgaaatttca     2640
catcagttga tcatggcata tccaaagata aaagagacta tctgtggaca tctgccaaaa     2700
atactttatc tacaccattg ccaaaggcat atacagtgaa gacaccaaca aaaccaaaac     2760
tacagcaaag agaaaacttg aatatacccca ttgaagaaag taaaaaaaag agaaaaatgg     2820
cctttgaatt tgatattaat tcagatagtt cagaaactac tgatctttg agcatggttt     2880 cagaagaaga gacattgaaa acactgtata ggaacaataa tccaccagct tctcatcttt     2940
```

```
gtgtcaaaac accaaaaaag gccccttcat ctctaacaac ccctggatct acactgaagt    3000
ttggagctat aagaaaaatg cgggaggacc gttgggctgt aattgctaaa atggatagaa    3060
aaaaaaaact aaaagaagct gaaaagttat ttgtttaatt tcagagaatc agtgtagtta    3120
aggagcctaa taacgtgaaa cttatagtta atattttgtt cttatttgcc agagccaaat    3180
tttatctgga agttgagact taaaaaatac ttgcatgaat gatttgtgtt tctttatatt    3240
tttagcctaa atgttaacta catattgtct ggaaacctgt cattgtattc agataattag    3300
atgattatat attgttgtta cttttttcttg tattcatgaa aactgttttt actaagtttt   3360
caaatttgta aagttagcct ttgaatgcta agaatgcatt attgagggtc attctttatt    3420
ctttactatt aaaatatttt ggatgc                                         3446

<210> SEQ ID NO 3
<211> LENGTH: 457
<212> TYPE: DNA
<213> ORGANISM: Homo sapien
<220> FEATURE:
<223> OTHER INFORMATION:

<400> SEQUENCE: 3
agcttcccaa aaaatgttcg ctaaccttt tcatasttt agaccattac aaratataaa       60
tagcaaagtc aactggaatt gtaattarag ctttgatttt tcttgggcta raggttttt     120 ctgccattct gatraaccct ggaggaaggg ascaaggtcg gcgggatttg gccgaggggc    180
ggggtgagga ctgcgcaggc tcascttctc agctggaaga ggaagtcccg agtgcaggcg   240
tctgcggccc ccatggtgac cagaccgact tccgcccgac ccgcccacct ctaccggccc   300
ctaatcccgc gaggcgcacc atggcaacca gacttctgcg tcgcggaagc gggtcccgca   360
ggtcgccacg gttgggggaa acgcggcgga cgccgccccc gtcccgaagg ggactcgaaa   420
atgtacagcc agcggtttgg caccgtacag cgggagg                            457
```

METHODS FOR DETECTION OF DISEASE-ASSOCIATED ANTIBODIES IN URINE

The present application claims the benefit of priority of U.S. Provisional Application Ser. No. 60/300,258 filed on Jun. 22, 2001, the contents of which are incorporated herein by reference.

FIELD OF THE INVENTION

This invention relates to methods of detecting disease-associated antibodies in patient urine. These methods allow the status of a disorder in a patient characterized by aberrant expression of a naturally occurring protein to be monitored. The present invention also relates to diagnostic kits. The present invention also relates to methods of identifying disease-associated markers.

BACKGROUND AND PRIOR ART

1. Introduction

It is well established that many pathological conditions, including but not limited to infections, cancer, and autoimmune disorders, are characterized by aberrant expression of certain molecules. It is also known that the altered expression of these molecules leads to the induction of a humoral-immune response and the production of circulating antibodies against those molecules. Both the disease-associated molecules and the presence of serum antibodies are useful "markers" for the detection and monitoring of particular pathologies and for the generation of diagnostic and/or therapeutic agents.

2. Detection of Disease-associated Antibodies in Patient Samples

Although accurate assays for determining the presence of disease markers in a subject are commercially available, these assays rely on the detection of serum antibodies against particular markers and are both complex and inconvenient. There has long been a need for non-invasive, simple assays for antibodies specific for the presence of disease markers. Assays that rely on the detection of specific antibodies in urine, for example, are non-invasive, require less sample preparation and are generally less complex than serum-based assays. High-titer antibody responses have been detected in both serum and urine of HIV-, *Helicobacter pylori*-, *Schistosoma mansoni*-, *Schistosoma haematobium*-, and *Schistosoma japonicum*-infected individuals. (Wu et al. (2001) *Hepatogastroenterology* 48: 614–7; Zhu et al. (2000) *Diagn. Microbiol. Infect. Dis.* 38: 237–41; Yamamoto et al. (2000) *Helicobacter* 5: 160–4; Bauer et al. (1992) *Lancet* 340: 559). A strong correlation between serum-antibody and urine-antibody levels, combined with the beneficial features of urine-based assays compared to serum-dependent tests, makes urine-based diagnostics particularly attractive. Although the presence of antibody against infectious agents in urine has been reported (Wu et al. (2001) *Hepatogastroenterology* 48: 614–7; Zhu et al. (2000) *Diagn. Microbiol. Infect. Dis.* 38: 237–41; Yamamoto et al. (2000) *Helicobacter* 5: 160–4; Bauer et al. (1992) *Lancet* 340: 559), the utility of these methods for the detection of antibodies against autologous molecules such as tumor-associated antigens and self-antigens, in diagnostic methods for cancer or autoimmune disease, has never been demonstrated.

Both humoral- and cellular-immune responses against human tumor-associated antigens have been observed in patients with different types of cancer (Knuth et al. (1984) *Proc. Natl. Acad. Sci. USA* 81: 3511–5; Sahin et al. (1995) *Proc. Natl. Acad. Sci. USA* 92: 11810–3). Based on the specific recognition by humoral and/or cellular effectors of the immune system, a large number of tumor-associated antigens—and thus, likely diagnostic reagents—have been identified (Knuth et al. (1984) *Proc. Natl. Acad. Sci. USA* 81: 3511–5; Old (1981) *Cancer Res.* 41: 361–75; Angelopoulou et al. (1994) *Int. J. Cancer* 58: 480–7; Jager et al. (1998) *J. Exp. Med.* 187: 265–70; Tureci et al. (1997) *Mol. Med. Today* 3: 342–9). These antigens can be categorized into six groups according to their expression patterns, function or origin. Specifically, these groups include: a) Cancer-Testis (CT) antigens, which are expressed in normal germ cells and aberrantly expressed in different tumors (van der Bruggen et al. (1991) *Science* 254: 1643–7; Tureci et al. (1998) *Proc. Natl. Sci. USA* 95: 5211–6; Gure et al. (2000) *Int. J. Cancer* 85: 726–32; Gure et al. (1997) *Int. J. Cancer* 72: 965–71; Chen et al. (1997) *Proc. Natl. Acad. Sci. USA* 94: 1914–8); b) differentiation antigens, which are expressed in tumor cells and the corresponding normal tissue of origin (Brichard et al. (1993) *J. Exp. Med.* 178: 489–95; Kawakami et al. (1994) *Proc. Natl. Acad. Sci. USA* 91: 3515–9; Kawakami et al. (1994) *Proc. Natl. Acad. Sci. USA* 91: 6458–62; Jager et al. (2001) *Cancer Res.* 61: 2055–61); c) mutated normal genes (Disis et al. (1997) *Adv. Cancer Res.* 71: 343–71; Coulie et al. (1995) *Proc. Natl. Acad. Sci. USA* 92: 7976–80; Wolfel et al. (1995) *Science* 269: 1281–4); d) overexpressed 'self' antigens (Disis et al. (1997) *Adv. Cancer Res.* 71: 343–71; Gnjatic et al. (1998) *J. Immunol.* 160: 328–33); e) viral antigens (Lennette et al. (1995) *Eur. J. Cancer* B31A: 1875–8; Tindle et al. (1996) *Curr. Opin. Immunol.* 8: 643–50); and f) splice variants of normal genes (Scanlan et al. (1998) *Int. J. Cancer* 76: 652–8; Jager et al. (1999) *Cancer Res.* 59: 6197–204).

The CT antigen NY-ESO-1, initially identified by serological expression cloning of a recombinant cDNA library obtained from a squamous cell carcinoma of the esophagus, elicits both humoral- and cellular immune responses in patients with NY-ESO-1-positive cancers (Chen et al. (1997) *Proc. Natl. Acad. Sci. USA* 94: 1914–8; Jager et al. (1998) *J. Exp. Med.* 187: 265–70; Jager et al. (1999) *Int. J. Cancer* 84: 506–10; Stockert et al. (1998) *J. Exp. Med.* 187: 1349–54). NY-ESO-1 serum antibody is a reliable indicator of CD4- and CD8-positive T-cell responses against NY-ESO-1-derived peptide epitopes presented by different MHC class I and class II alleles (Chen et al. (1997) *Proc. Natl. Acad. Sci. USA* 94: 1914–8; Jager et al. (2000) *Proc. Natl. Acad. Sci. USA* 97: 4760–5; Jager et al. (2000) *J. Exp. Med.* 191: 625–30). High-titer NY-ESO-1 serum antibody was found in patients with advanced NY-ESO-1-positive malignancies. Changes in NY-ESO-1 antibody titers over extended periods of time correlate with the clinical development of NY-ESO-1-positive disease (Jager et al. (1998) *J. Exp. Med.* 187: 265–70).

As with NY-ESO-1, other tumor-associated antigens have been shown to elicit both humoral and cellular immune responses that are demonstrated by detection of both autologous antibodies and T cells in cancer patients. Examples of these tumor-associated antigens are SSX2 (Ayyoub et al. (2002) *J. Immunol.* 168: 1717–1722; Sahin et al. (1995) *Proc. Nat'l. Acad. Sci. USA* 92: 11810–11813; both incorporated herein by reference), MAGE-1 (Sahin et al. (1995) *Proc. Nat'l. Acad. Sci. USA* 92: 11810–11813; van der Bruggen et al. (1991) *Science* 254: 1643–1647; both incorporated herein by reference) and tyrosinase (Sahin et al. (1995) *Proc. Nat'l. Acad. Sci. USA* 92: 11810–11813; Brichard et al. (1993) *J. Exp. Med.* 173: 489–495; both incorporated herein by reference). In view of the finding that disease specific antibodies are detected in the urine of patients infected with various organisms (Wu et al. (2001) *Hepatogastroenterology* 48: 614–7; Zhu et al. (2000) *Diagn. Microbiol. Infect. Dis.* 38: 237–41; Yamamoto et al. (2000) *Helicobacter* 5: 160–4; Bauer et al. (1992) *Lancet* 340: 559), and the finding that—in addition to activating cellular immunity—tumor-associated antigens induce production of detectable levels of serum antibody, the inventors investigated whether aberrations in the expression of autologous proteins in non-infectious diseases and disorders, such as tumor-associated antigens, result in the excretion of antibodies urine. The results of these investigations provide the basis for the development of urine-based tests for the detection and monitoring of spontaneous and vaccine-induced immunity against defined disease-associated antigens in patients suffering from disorders characterized by the aberrant expression of the antigen.

The present invention demonstrates that specific antibodies against an aberrantly expressed molecule can be detected in urine samples taken from patients believed to be expressing that molecule, and that these molecules and their derivatives are useful diagnostic and therapeutic reagents. This discovery has important implications for the detection and monitoring of spontaneous and vaccine-induced immunity against defined disease-associated antigens.

3. Identification of Disease-associated Antigens: SEREX

The identification and preparation of disease-associated antigens is laborious, unpredictable and expensive. Two main methods have been used for the detection of such antigens. In the gene-based approach, host cells are transformed or transfected with a tumor-derived cDNA library and tested for the expression of the specific antigen. See, e.g., dePlaen et al. (1988) *Proc. Natl. Sci. USA* 85: 2275; incorporated herein by reference. In contrast, the biochemical approach is based on the elution of peptides from MHC-class I molecules of tumor cells, followed by isolation and purification of those peptides by reverse-phase high performance liquid chromatography (RP-HPLC) and testing for the ability of the peptides to bind MHC-class I molecules and activate cytotoxic T-lymphocytes (CTLs), including induction of CTL proliferation, release of tumor necrosis factor (TNF), and the lysis of target cells. The disadvantages of these approaches are highlighted by the relatively few new antigens identified by these methods. See, e.g., van der Bruggen et al. (1991) *Science* 254: 1643–1647; Brichard et al. (1993) *J. Exp. Med.* 178: 489–495; Coulie, et al. (1994) *J. Exp. Med.* 180: 35–42; Kawakami et al. (1994) *Proc. Natl. Acad. Sci. USA* 91: 3515–3519. Furthermore, these methods require established, permanent tumor-cell lines of the cancer type under consideration. Stable tumor-cell lines are very difficult to establish and maintain. See, e.g., Oettgen et al. (1990) *Immunol. Allerg. Clin. North. Am.* 10: 607–637. Also, numerous tumor types, including epithelial cell-tumors, are not responsive to CTLs in vitro, thereby precluding routine assay. These problems have led to the development of new methods for identifying disease-associated antigens.

The SEREX method ("Serological identification of antigens by Recombinant Expression Cloning") has been used to both identify new disease-associated antigens and confirm expression of previously identified antigens. Sahin et al. (1995) *Proc. Natl. Acad. Sci. USA* 92: 11810–11913; Crew et al. (1995) *EMBO J.* 144: 2333–2340; U.S. Pat. Nos. 5,698,396; 6,251,603; and 6,252,052; each incorporated herein by reference. In brief, the SEREX method involves the expression of tumor-derived cDNA libraries in a prokaryotic host followed by screening with absorbed and diluted sera. The binding of serum antibodies to the expressed protein antigens identifies those proteins as antigens likely to elicit a high titer humoral-immune response. SEREX has led to the identification, isolation and cloning of a large number of immunogenic molecules that induce autologous humoral antibody responses. Several of these molecules have also been shown to induce autologous T-cell responses. NY-ESO-1 was identified by SEREX using serum from a patient with an esophageal tumor. See, e.g., U.S. Pat. Nos. 5,698,396; 6,251,603; 6,252,052; and U.S. patent application Ser. No. 09/062,422; each incorporated herein by reference. SEREX has also been used to monitor the status of a disease or disorder by assaying for antibodies specific to that disease or disorder. See, e.g., U.S. Pat. Nos. 5,698,396; 6,251,603; 6,252,052; and U.S. patent application Ser. No. 09/062,422 each incorporated herein by reference.

The search for disease- and tumor-associated antigens may be improved by screening disease- and tumor-derived cDNA expression libraries with autologous or allogeneic urine samples. The inventors have demonstrated that urine represents a source of highly specific, high-titer antibodies that are useful in diagnostic and therapeutic applications and in methods for identifying new disease-associated antigens.

SUMMARY OF THE INVENTION

The present invention provides methods for determining whether a patient suffers from a disorder characterized by aberrant expression of a naturally occurring gene, comprising: i) contacting a sample containing urine from a patient that is believed to suffer from said disorder with an agent that specifically binds to an antibody present in said urine and characteristic of said condition, under conditions favoring complex formation between the agent and the antibody; and ii) detecting the described complex, wherein detection of the complex indicates that the patient suffers from said disorder. In one embodiment, the agent is a cell that presents a binding partner for said antibody on its surface. In another embodiment, the agent is a binding partner for said antibody and is not cell-associated. In a preferred embodiment, the agent is a tumor-associated antigen. The tumor-associated antigens of the present invention include antigens identified by SEREX. The tumor-associated antigen of the present invention preferably induces the production of a cellular-immune response and/or a humoral-immune response. More preferably, the tumor-associated antigen is a cancer-testis (CT) antigen, a differentiation antigen, a mutated normal gene, an overexpressed self antigen, or a viral antigen. In a preferred embodiment the tumor-associated antigen is NY-ESO-1 (SEQ ID NO: 1), NY-BR-1, (GenBank Accession Nos. XM165546 and XM16671 1 (both version 1 and submitted May 13, 2002); Cross et al. (2000) *Mamm. Genome* 11(5): 373–383; all incorporated herein by reference), SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference) and UniGene designation Hs.339651 or the clone 18CGI1F2 (SEQ ID NO: 3; GenBank Accession No. AJ236609 (May 2, 2000; version 1) and the UniGene designation Hs.33965 1; both incorporated herein by reference). Most preferably, the tumor-associated antigen is NY-ESO-1 (SEQ ID NO: 1).

The present invention also provides a method for monitoring the status of a disorder in a patient characterized by aberrant expression of a naturally occurring gene, comprising: i) contacting a sample containing urine from a patient that is believed to suffer from said disorder with an agent that specifically binds to an antibody present in said urine and characteristic of said condition, under conditions favoring complex formation between the agent and the antibody; and ii) detecting the described complex; and iii) comparing a value obtained to a prior value obtained following assay of a prior sample taken from said patient, wherein any difference is indicative of a change in status of said disorder. In another embodiment, the agent is a binding partner for said antibody and is not cell-associated. In a preferred embodiment, the agent is a tumor-associated antigen. The tumor-associated antigens of the present invention include antigens identified by SEREX. The tumor-associated antigen of the present invention preferably induces the production of a cellular-immune response and/or a humoral-immune response. More preferably, the tumor-associated antigen is a cancer-testis (CT) antigen, a differentiation antigen, a mutated normal gene, an overexpressed self antigen, or a viral antigen. In a preferred embodiment the tumor-associated antigen is NY-ESO-1 (SEQ ID NO: 1), NY-BR-1, (GenBank Accession Nos. XM165546 and XM166711 (both version 1 and submitted May 13, 2002); Cross et al. (2000) *Mamm. Genome* 11(5): 373–383; all incorporated herein by reference), SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference) or the clone 18CGI1F2 (SEQ ID NO: 3; GenBank Accession No. AJ236609 (May 2, 2000; version 1) and the UniGene designation Hs.339651; both incorporated herein by reference). Most preferably, the tumor-associated antigen is NY-ESO-1 (SEQ ID NO: 1).

In one embodiment of the present invention, the complex between the tumor-associated antigen and the antibody is detected by a Western Blot. In a preferred embodiment, the described complex is detected by the specific binding of a second antibody to the antibody of the complex. The second antibody specifically binds any portion of the antibody present in the urine of the patient when it is complexed with an agent. This antibody preferably binds the $F_c$ portion of the antibody of the described complex. For example, if the antibody of the complex is human, the second antibody may be an antibody that specifically binds human antibodies. In one embodiment, the antibody that specifically binds the antibody present in the urine of a patient contains a detectable label. In a preferred embodiment, the detectable label includes fluorescent molecules, radioactive molecules, proteins, magnetic beads, or metals. In a more preferred embodiment, the complex between the tumor-associated antigen and the antibody is detected by an enzyme-linked immunosorbent assay (ELISA).

In another embodiment of the present invention, the agent or the second antibody is immobilized on a solid matrix. The solid matrix may be plastic, glass, paper, nitrocellulose, nylon, poly(vinyl-chloride), cellulose, polyacrylamide, polystyrene or polypropylene. In a preferred embodiment, the solid matrix is a magnetic bead.

The present invention also provides a kit comprising: i) an agent that binds an antibody present in urine of a patient suffering from a disorder characterized by aberrant expression of a naturally occurring gene; and ii) a second component selected from the group consisting of: a control antibody, a control antigen, a positive control sample containing urine, a negative control sample containing urine, an antibody that specifically binds the antibody present in the urine of said patient, and instructions for use of the agent for the detection of an antibody that is present in urine and specifically binds to the agent. In the kits of the present invention, the preferred agent is a tumor-associated antigen. More preferably, the tumor-associated antigen is NY-ESO-1 (SEQ ID NO: 1) SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference), NY-BR-1, (GenBank Accession Nos. XM165546 and XM16671 1 (both version 1 and submitted May 13, 2002); Cross et al. (2000) *Mamm. Genome* 11(5): 373–383; all incorporated herein by reference) or clone 18CGI1F2 (SEQ ID NO: 3; GenBank Accession No. AJ236609 (May 2, 2000; version 1) and the UniGene designation Hs.339651; both incorporated herein by reference). Most preferably, the tumor-associated antigen is NY-ESO-1 (SEQ ID NO: 1).

In another embodiment, the kits of the present invention further comprise an antibody that specifically binds the antibody present in the urine of a patient suffering from a disorder. In a preferred embodiment, the antibody that specifically binds the antibody present in the urine of a patient suffering from a disorder contains a detectable label. In a more preferred embodiment the label is a fluorescent molecule, a radioactive molecule, a protein, a magnetic bead, or a metal.

In another embodiment, the kits of the present invention contain an agent that is immobilized on a solid matrix. In yet another embodiment, the kits of the present invention contain an antibody that specifically binds the antibody present in the urine of a patient suffering from a disorder, wherein that antibody is immobilized on a solid matrix. In a preferred embodiment, the solid matrix is plastic, glass, paper, nitrocellulose, nylon, poly(vinyl-chloride), cellulose, polyacrylamide, polystyrene, or polypropylene. In a more preferred embodiment, the solid matrix is a magnetic bead.

The present invention also provides a method for determining an immunoreactive substance produced by a subject, wherein said subject is capable of eliciting an immune response, comprising: i) producing a cDNA library from a cell taken from said subject; ii) inserting said cDNA library into an expression vector; iii) transfecting said vector into a host cell to produce a transfected host cell; iv) culturing said transfected host cell to express said immunoreactive substance; v) contacting a urine sample which contains an antibody specific to said immunoreactive substance with a sample of non-transfected host cells, to remove an immunologic binding partner from said sample which is specific for said non-transfected host cell, to produce a stripped urine sample; vi) contacting said stripped urine sample with a sample of host cells transfected with the same vector into which said cDNA library has been inserted, wherein said vector does not contain any library cDNA, to remove any immunologic binding partners specific for vector produced antigens thereby producing a twice stripped urine sample; vii) contacting said twice stripped urine sample to the transfected host cell of (iv), thereby any immunologic binding partners specific for said immunoreactive substance bind thereto; and vii) determining binding in (vii) to determine said immunoreactive substance. In a preferred embodiment, the cultured transfected cell of step (iv) is lysed to produce cell lysate and said cell lysate is contacted with urine as in step (v). In one embodiment of the present invention the immunoreactive substance is a tumor-associated antigen. In a preferred embodiment, the immunoreactive substance is an autoimmune-disease-associated antigen.

DETAILED DESCRIPTION OF THE INVENTION

As used herein the term "agent that specifically binds to an antibody" refers to a binding partner of an antibody present in serum or urine. The agents of the present invention specifically bind to the antigen-binding portion of an antibody present in serum or urine. Agents include, but are not limited to, antigens and antibody-binding fragments thereof—either naturally occurring or recombinant or engineered—cells expressing antigens and antibody-binding fragments thereof. Agents may be molecules which are or contain protein, carbohydrate, nucleic acid, or any compound that mimics the structure of a binding partner of an antibody present in patient serum or urine.

In one embodiment of the present invention, the agent is a cell that presents a molecule on its surface that is a binding partner for an antibody present in the urine of a patient suffering from a disease or disorder characterized by aberrant expression of a naturally occurring gene. In this embodiment, cells are first contacted with urine that may contain an antibody that is specific for a molecule on the surface of the cell. Detection of a complex between the cell and a urine antibody indicates that the patient's urine contains an antibody specific for a molecule on the surface of the cell and that the patient suffers from a disorder characterized by aberrant expression of a naturally occurring gene. The complex between an agent and an antibody present in the urine of a patient may be detected by the specific binding of a second antibody that specifically binds the urine antibody. The second antibody may contain a detectable label. This label may be attached directly or indirectly through a linker or conjugating agent such as glutaraldehyde, periodate, and the like. A wide variety of different conjugation techniques exist, which are well known to the skilled artisan. Cells labeled with a second antibody may be detected by flow cytometry.

The agents and antibodies of the disclosed kits may be formulated with acceptable carriers such that they can be used directly from the container without further preparation, in the kits of the present invention. Further, the agents and antibodies may be lyophilized with lyoprotective agents known in the art, such as trehalose and tricine, to enhance stability and increase shelf-life. Also, the container(s) may be presented in a pack or dispenser device. The pack or dispenser device may be accompanied by instructions for use of the agents and antibodies for determining that a patient suffers from a disorder characterized by aberrant expression of a naturally-occurring gene. The kits may also comprise additional materials necessary to conduct the assay, including but not limited control antibodies, control antigens, and/or materials necessary for calibration of the detector.

As used herein, the term "antibody", unless indicated otherwise, is used broadly to refer to both antibody molecules and a variety of antibody-derived molecules. Such antibody-derived molecules comprise at least one variable region (either a heavy chain of light chain variable region) and include molecules such as Fab fragments, F(ab)$_2$ fragments, single chain (sc) antibodies, diabodies, triabodies, tetrabodies, individual antibody light chains, individual antibody heavy chains, chimeric fusions between antibody chains and other molecules, and the like. As used herein, "antigen-binding fragment" or "antigen-binding domain" or "Fab fragment" refer to the about 45 kDa fragment obtained by papain digestion of an immunoglobulin molecule and consist of one intact light chain linked by disulfide bond to the N-terminal portion of the contiguous heavy chain. As used herein, "F(ab)$_2$ fragment" refers to the about 90 kDa protein produced by pepsin hydrolysis of an immunoglobulin molecule. It consists of the N-terminal pepsin cleavage product and contains both antigen binding fragments of a divalent immunoglobulin, such as IgD, IgE, and IgG. Neither the "antigen-binding fragment" nor "F(ab)$_2$ fragment" contain the about 50 kDa F$_c$ fragment produced by papain digestion of an immunoglobulin molecule that contains the C-terminal halves of the immunoglobulin heavy chains, which are linked by two disulfide bonds, and contain sites necessary for compliment fixation. The term, as used herein, also includes antibodies with engineered F$_c$ regions, such as humanized antibodies.

As used herein the term "antigen" refers to any molecule, substance or complex that stimulates the production of a specific antibody or antibodies when introduced into an immunocompetent animal.

As used herein, the term "autologous gene" or "autologous protein" refers to a gene or protein that is self-produced. A protein that is autologous to a subject is produced by that subject.

As used herein, the term "binding partner" refers to a molecule, compound or complex that will bind to another molecule, compound or complex, under the appropriate conditions in the presence of that molecule, compound or complex. Binding partners useful in the present invention include specific binding pairs such as antigens and antibodies, or fragments of antibodies, both polyclonal and monoclonal, lectins and carbohydrates, hormones and hormone receptors, enzymes and enzyme substrates, biotin and (strept) avidin vitamins and vitamin binding proteins, complementary polynucleotide sequences, drugs and receptors, enzymes and inhibitors, apoproteins and cofactors, growth factors and receptors, and the like. Biotin and (strept) avidin derivatives may also be used, including biotin analogs/avidin, biotin/streptavidin, and biotin analogs/streptavidin. Binding partners may be naturally occurring or "engineered." Such techniques are well known in the art, and include the design and production of chimeric and humanized antibodies and fragments thereof, synthetic peptides, modified enzymes or substrates, synthetic RNA and DNA oligonucleotides, and the like.

As used herein the term "cancer-testis (CT) antigen" refers to antigens that are exclusively expressed in a variety of tumors and normal germ cells. In a preferred embodiment, the CT antigens are selected from the group consisting of: the MAGE-family of proteins; the BAGE-family of proteins; the GAGE-family of proteins; the LAGE-family of proteins; NY-ESO-1 proteins; SSX, SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference), CT-10, clone 18CGI1F2 (SEQ ID NO: 3; GenBank Accession No. AJ236609 (May 2, 2000; version 1) and the UniGene designation Hs.33965 1; both incorporated herein by reference), and the like. In a more preferred embodiment the CT antigens are selected from the group consisting of: NY-ESO-1 (SEQ ID NO: 1), and SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference). The MAGE-family of proteins include MAGE-1, MAGE-2, MAGE-3, MAGE-4, MAGE-5, MAGE-6, MAGE-7, MAGE-8, MAGE-9, MAGE-10, MAGE-11, MAGE-12, MAGE-13, MAGE-Xp2 (MAGE-B2), MAGE-Xp3 (MAGE-B3), MAGE-Xp4 (MAGE-B4), MAGE-C1, MAGE-C2, and antibody-binding fragments thereof. The BAGE-family of proteins include BAGE-1, and antibody-binding fragments thereof. The GAGE-family of proteins include GAGE-1, GAGE-2, GAGE-3, GAGE4, GAGE-5, GAGE-6, GAGE-7, GAGE-8 and antibody-binding fragments thereof. The RAGE-family of proteins include RAGE-1, and antibody-binding fragments thereof. The LAGE-family of proteins include LAGE-1, and antibody-binding fragments thereof. The PRAME-family of proteins includes PRAME-1, and antibody-binding fragments thereof. NY-ESO-1 includes NY-ESO-1 (SEQ ID NO: 1) and antibody-binding fragments thereof. CT7 includes CT7 and antigen-binding fragments thereof. The SSX-family of proteins includes SSX-1, SSX-2 (HOM-MEL-40), SSX-4, SSX-5 and anitbody-binding fragments thereof. The OY-TES-1-family of proteins includes OY-TES-1 and antibody-binding fragments thereof.

As used herein the term "complex" refers to a combination of two or more molecules that have spatial and/or polar features that permit specific binding to each other. Examples of complexes of the present invention include ligand-receptor complexes, enzyme-substrate complexes, protein-protein complexes, and agent-antibody complexes, and the like. Binding may be either covalent or non-covalent.

As used herein, the term "a control antibody" refers to an antibody that binds a particular agent, under conditions favoring the formation of an agent-antibody complex (positive control) or does not bind a particular agent, under conditions favoring the formation of an agent-antibody complex (negative control).

As used herein, the term "a control antigen" refers to an antigen that binds a particular antibody, under conditions favoring the formation of an antigen-antibody complex (positive control) or does not bind a particular antibody, under conditions favoring the formation of an antigen-antibody complex (negative control).

As used herein, the term "a positive control sample containing urine" refers to a urine sample that contains an antibody that specifically binds a defined agent, under conditions favoring the formation of an antigen-antibody complex. Specifically, in a kit of the present invention, "a positive control sample containing urine" refers to a urine sample that contains an antibody that specifically binds the agent provided in the kit, under conditions favoring the formation of an antigen-antibody complex.

As used herein, the term "a negative control sample containing urine" refers to a urine sample that contains an antibody that does not specifically bind a defined agent, under conditions favoring the formation of an antigen-antibody complex. Specifically, in a kit of the present invention, "a negative control sample containing urine" refers to a urine sample that does not specifically bind the agent provided in the kit.

As used herein the term "detecting the complex" or "detection of the complex" refers to the ability to identify the formation of a complex between an agent and an antibody. Any method of detection or assay for detecting the presence and/or formation of a complex is contemplated by the present invention. Such assays include but are not limited to heterogeneous- or homogeneous-phase assays, such as sandwich assays, radioimmunoassays, enzyme-linked immunosorbent assays (ELISA), fluorescent immunoassays, protein A immunoassays, nephelometric assays, etc. In a preferred embodiment, the method of detection is Western blotting.

In another embodiment, the complex between an agent and an antibody present in the urine of a patient may be detected by the specific binding of a second antibody that specifically binds the urine antibody. The second antibody may contain a detectable label. This label may be attached directly or indirectly through a linker or conjugating agent such as glutaraldehyde, periodate, and the like. A wide variety of different conjugation techniques exist, which are well known to the skilled artisan. Such detectable labels include, but are not limited to: radioactive moieties, substrate-converting enzymes, such as horseradish peroxidase, glucose oxidase, .beta.-galactosidase, alkaline phosphatase, and the like, fluorophores, biotin, proteins, magnetic beads, metals, and the like. See, e.g., *Antibodies: A Laboratory Manual*, Harlow et al. (1988) Cold Spring Harbor Laboratory Press, Cold Spring Harbor, N.Y.; incorporated herein by reference.

In a preferred embodiment, the method of detection of the agent-antibody complexes is magnetic separation using antibody-coated or agent-coated magnetic beads. Kemmner et al. (1992) *J. Immunol. Methods* 147: 197–200; Racila et al. (1998) *Proc. Natl. Acad. Sci. USA* 95: 4589–4594. The antibody used to coat the magnetic bead specifically binds the antibody isolated from patient urine or serum.

As used herein the term "a differentiation antigen" refers to any cell-surface antigen—a molecule that stimulates the production of antibodies specific to that molecule—wherein the expression of that molecule varies during successive developmental stages of a particular cell type. Differentiation antigens include tyrosinase, brain glycogen phosphorylase, Melan-A, NY-BR-1 (GenBank Accession Nos. XM165546 and XM166711 (both version 1 and submitted May 13, 2002); Cross et al. (2000) *Mamm. Genome* 11(5): 373–383; all incorporated herein by reference) or clone 18CGI1F2 (SEQ ID NO: 3; GenBank Accession No. AJ236609 (May 2, 2000; version 1) and the UniGene designation Hs.339651; both incorporated herein by reference), MART-1, gp100, TRP-1, TRP-2, etc., and antibody-binding fragments thereof.

As used herein the term "disease-associated antigen or disease-associated marker" refers to any specific molecule that corresponds to a disease or disorder, and that may be detected by a genetic or biochemical test.

As used herein the term "a disorder characterized by aberrant expression of a naturally occurring gene" refers to a disease or disorder produced by altered expression of one or more genes or the presence of one or more proteins. These genes and proteins may be naturally occurring, mutated, autologous or derived from a different organism.

As used herein, the term "high serum-antibody titer" refers to a serum sample that produces a strong band on a Western blot, when the serum is diluted 1000-fold.

As used herein, "high urine-antibody titer" refers to a urine sample that produces a strong band on a Western blot, when the urine is 100-fold diluted.

As used herein the term "immobilized" refers to attachment of an agent or antibody of the present invention to a solid matrix. Covalent attachment includes attachment through the N- or C-terminus or any other amino acid residue, carbohydrate or other moiety. The antigens or antibodies of the present invention may be attached directly or through a linker or conjugating agent. The term also refers to the inability of the immobilized agent or antibody to diffuse into and through the solvent, fluid or reagent.

As used herein, the term "immunoreactive substance" refers to any substance that binds to the antigen-binding domain of an antibody or stimulates a humoral or cellular immune response.

As used herein the term "label" refers to a molecule that directly or indirectly mediates the production of a signal that is indicative of the presence or absence of a specific antibody in the urine sample. A label may be attached directly or indirectly through a linker or conjugating agent such as glutaraldehyde, periodate, and the like. A wide variety of different conjugation techniques exist, which are well known to the skilled artisan. Labels may include enzymes, fluorescent molecules, metal sols, colored latex spheres, colloidal metals, magnetic beads and those disclosed in U.S. Pat. Nos. 4,954,452; 4,313,734; 5,252,459; 4,373,932; and 4,703,013; each incorporated by reference herein in their entirety. See, e.g., *Antibodies: A Laboratory Manual*, Harlow et al. (1988) Cold Spring Harbor Laboratory Press, Cold Spring Harbor, N.Y. Colored latex particles are described in U.S. Pat. No. 4,703,017, which is incorporated herein by reference in its entirety. The label may also be an inducible property of the particles, such as colorable latex particles. See, e.g., U.S. Pat. Nos. 4,373,932; 4,837,168; both incorporated herein by reference in their entirety. Metal labels include metal or metal compounds such as metal oxides, metal hydroxides, metal salts or polymer nuclei coated with a metal or metal compound. These metal labels may include dry forms of any of the above-named metals or metal compounds, and include colloidal gold in dry form. For example, the metal label can be composed of a metal sol, a selenium sol or a carbon sol. See, e.g., U.S. Pat. Nos. 4,313,734; 4,775,636; 4,954,452; and 5,559,041; each incorporated herein by reference in their entirety.

In a preferred embodiment, the agent-antibody complex is detected by an ELISA assay. The ELISA assays of the present invention may use any number of different enzymes, such as horseradish peroxidase, glucose oxidase, beta.-galactosidase, alkaline phosphatase, and the like. Enzymes suitable for ELISA assays are well known in the art. Suitable substrates corresponding to a specific enzyme is generally chosen for the production, upon hydrolysis by the corresponding enzyme, of a product that is either colored and detectable by visible spectrometry, or is colorless and detectable by UV spectrometry. For example, p-nitrophenyl phosphate is suitable for use with alkaline phosphatase conjugates; for peroxidase conjugates, 1,2-phenylenediamine or tetramethylbenzidine are commonly used. Fluorogenic substrates that produce a fluorescent product may also be used. These fluorogenic substrates include substrates labeled directly or indirectly with fluorescein or rhodamine. In all cases, the enzyme-labeled second antibody is added to the agent-antibody complex. A solution containing the appropriate substrate is then added to the tertiary complex of antibody-antigen-labeled second antibody complex. The substrate reacts with the enzyme linked to the antibody, giving a signal that correlates to the amount of antibody present in the patient's urine.

As used herein the term "marker" refers to any specific molecule that corresponds to a specific characteristic, state or quality, and that may be detected by a genetic or biochemical test.

As used herein the term "a mutated normal gene" refers to a gene and its corresponding product, wherein the normally-occurring gene has been mutated to alter the expression of the mutated gene or another gene, alter the differentiation state of the cell, or that leads to the development of unregulated growth or division of the cell. Mutated normal genes and proteins include MUM-1, CDK4, NAG, β-catenin, gp-100-in4, p15, etc., and antibody-binding fragments thereof.

As used herein the term "naturally-occurring gene" or "naturally-occurring protein" refers to a gene or protein that is endogenous to a cell. Naturally-occurring genes and proteins include mutated forms that lose function or biological activity, or retain function or biological activity.

As used herein the term "an overexpressed self antigen" refers to an antigen that is present in a subject's own cells or tissues and is overexpressed. As used herein, this term also refers to self antigens that are expressed at normal levels or below normal levels where autologous antibodies are produces against the antigen.

As used herein the term "solid matrix" refers to any solid material of any size, shape, composition or construction that is suitable as an attachment material for any agent or antibody of the present invention. The solid matrix is preferably poly(vinyl-chloride), but may be other polymers such as cellulose, polyacrylamide, nylon, polystyrene or polypropylene. The solid matrix may be in the form of tubes, beads, discs or micro plates, or any other surfaces suitable for conducting an assay. Any agent or antibody of the present invention may be covalently or non-covalently attached to the solid matrix. Covalent attachment includes attachment through the N- or C-terminus or any other amino acid residue, carbohydrate or other moiety. The antigens or antibodies of the present invention may be attached directly or through a linker or conjugating agent. Methods of attaching molecules to a solid matrix are well known in the art and include treatment of the molecule or the solid matrix with CNBr, carbonyldimidazole, tresyl chloride and the like.

In a preferred embodiment, the solid-matrix is contained in a dip-stick device that allows for the direct assay of a patient's urine. This device may be placed into a urine stream or dipped into a previously collected urine sample. In known devices, the test fluid wicks up through an absorbent membrane that is contact with the reagents that detect an analyte in the fluid. An example of such a device that is designed to reduce artifacts, such as flow and leading edge effects, is described in U.S. Pat. No. 6,372,514, which is incorporated herein by reference in its entirety. See also, U.S. Pat. Nos. 5,656,503 and 4,200,690; both incorporated herein by reference in its entirety. Reagents suitable in the detection of an agent-antibody complex in such an assay format are described in detail in: U.S. Pat. Nos. 4,861,711; 4,271,140; 5,622,871; 5,656,503; 5,602,040; and 5,591,645; each incorporated by reference herein in their entirety.

As used herein, the term "specifically binds" refers to the ability of an antibody to bind an agent, wherein that binding depends on the specific structure and properties of the antibody and the agent. "Specific binding" excludes all non-specific binding which does not depend on the particular structure and/or properties of the antibody and agent and the specific relationship between the agent and antibody.

As used herein, the term "specifically binds the antibody present in the urine of the patient" refers to the ability of an antibody to specifically bind any portion of the antibody present in urine, when it is complexed with an agent of the present invention. Preferably, this antibody binds the $F_c$ portion of the antibody of the described complex. "Specific binding" excludes all non-specific binding which does not depend on the particular structure and/or properties of the antibody and agent and the specific relationship between the agent and antibody.

As used herein the term "tumor-associated antigen" refers to an antigen that is differentially expressed on cancerous cells and tissues and not on the corresponding non-cancerous cell or tissue. The tumor-associated antigens of the present invention include antigens identified by SEREX. The tumor-associated antigen of the present invention preferably induces the production of a cellular-immune response and/or a humoral-immune response. Tumor-associated antigens include members of the cancer-testis (CT) antigen family; differentiation antigens; mutated normal genes; overexpressed self antigens; and viral antigens.

As used herein, the term "a viral antigen" refers to an antigen that is encoded by a viral genome and includes those virally encoded proteins that are post-translationally modified by the infected-host cell. The "viral antigen" or "viral antigens" of the present invention are limited to those antigens produced by oncogenic viruses, such as human papilloma virus (HPV), Epstein-Barr Virus (EBV), etc. As used herein, "viral antigen" specifically excludes any antigen produced by HIV.

EXAMPLES

The terms and expressions employed in the following Examples are used as terms of description and not of limitation. There is no intention of excluding any equivalents of the features shown and described. It is recognized that various modifications are possible within the scope of the invention.

Example 1

Immunoblot Analysis

Serum and urine antibody responses against the recombinant NY-ESO-1 protein were assayed by standard Western blot analysis (Towbin et al. (1979) *Proc. Natl. Acad. Sci. USA* 76: 4350–4). Briefly, 1 μg of purified recombinant NY-ESO-1 protein was diluted in SDS, and electrophoresed on a 15% SDS gel. In all assays, the recombinant NY-ESO-1 'short' protein—corresponding to amino acid positions 10–121 and a molecular weight of 14 kDa—was used. Full length and recombinant NY-ESO-1 'short' protein are both recognized by serum antibodies. After overnight blotting on a nitrocellulose filter (0.45 μm) and blocking with 3% BSA, blots were incubated with patient sera at 1:250, 1:1000, 1:5000, 1:10.000, 1:50.000, and 1:100.000 dilution. Dilutions with patient urine were 1:1 (undiluted), 1:250, and 1:1.000. The E978 mouse monoclonal antibody against NY-ESO-1 was used as a positive control. Binding of recombinant NY-ESO-1 'short' protein by serum and urine antibodies correlates with the binding of the naturally-expressed NY-ESO-1 protein (26 kDa)(expressed in the melanoma cell line NW-MEL-38) and the full-length recombinant NY-ESO-1 expressed in COS-7-transfected cells. Serum and urine antibodies binding to NY-ESO-1 were detected by incubation with goat anti-human IgG (Fc-spec.) 1:10.000, or goat anti-mouse IgG 1:3000, and visualized with NBT/X-phosphate. Serum and urine samples were considered positive for NY-ESO-1 antibody with a detectable 14 kDa protein band (recombinant NY-ESO-1 'short' protein) and a 26 kDa protein band (naturally-expressed NY-ESO-1 and full-length recombinant NY-ESO-1).

Example 2

ELISA

Recombinant NY-ESO-1 'short' protein at a concentration of 1 μg/ml in coating buffer (15 mM $Na_2CO_3$, 30 mM $NaHCO_3$, pH 9.6, with 0.02% $NaN_3$) was adsorbed to microwell plates 60×10 at 10 μl/well overnight at 4° C. Plates were washed with PBS, and blocked overnight at 4° C. with 10 μl/well of 2% BSA/PBS. After washing, 10 μl/well of serum and urine dilutions in 2% BSA was added and incubated for 2 h at room temperature. Plates were washed and 10 μl/well diluted secondary antibody in 2% BSA was added (Goat anti-human IgG-AP). The second antibody was incubated for 1 hour at room temperature. Plates were washed, incubated with 10 μl/well substrate solution for 25 minutes at room temperature, and immediately read. Serum and urine were tested over a four-fold range of dilutions—1:1, 1:100 to 1:100.000. (Stockert et al. (1998) *J. Exp. Med.* 187: 1349–54).

NY-ESO-1 urine antibody was detected in cancer patients, who had a high-titer serum reactivity. Nephropathy as a possible reason for increased renal protein loss was excluded in all patients, because none of the cancer patients exhibited decreased renal function. Strong NY-ESO-1 antibody reactivity that is detectable in patient urine is indicative of NY-ESO-1-specific CD8-positive T-cell reactivity. In contrast, none of the patients with weak or negative NY-ESO-1 serum and negative urine antibody had detectable CD8-positive T-cell reactivity. In the series of patients analyzed, there was no relation between the extent or location of NY-ESO-1 metastatic sites and NY-ESO-1 serum- and urine-antibody status. Changes in baseline NY-ESO-1 antibody reactivity, however, are associated with the clinical evolution of metastatic disease, and may be easily monitored by testing urine samples over time.

Example 3

High Serum NY-ESO-1-Antibody Titer Correlates with Detectable Urine NY-ESO-1 Antibodies Urine and serum samples from patients previously diagnosed with NY-ESO-1 -positive cancer were assayed for NY-ESO-1-specific antibodies. Patient tissue was typed to determine if their tumors expressed NY-ESO-1. Tumor typing for NY-ESO-1 is described in U.S. Pat. No. 5,804, 381, which is incorporated herein by reference. Using this methodology, ten NY-ESO-1-positive patients were identified: three breast cancer patients, two with non-small-cell lung carcinoma, and one each of neuroendocrine carcinoma, melanoma, sarcoma, bladder and stomach. All patients were tested for renal function, and all were normal. No subjects showed any evidence of significant proteinuria.

Serum and urine samples from each patient were examined by Western blotting. Jäger et al. (1999) *Int. J. Cancer* 84: 506–570; Stockert et al. (1998) *J. Exp. Med* 187: 1349–1354; and U.S. Pat. No. 6,251,603 and U.S. patent application Ser. No. 09/262,422, filed Apr. 17, 1998; all of which are incorporated herein by reference. Each Western blot included full-length recombinant NY-ESO-1 protein, and recombinant SSX protein—used as a negative control. The Western blots—also confirmed by ELISA—indicate that patients with a high serum NY-ESO-1-antibody titer—detectable band at a dilution of 1:1000—excrete NY-ESO-1 antibodies into urine at levels sufficient to produce a strong signal on Western blots. In low-titer serum samples, where NY-ESO-1 antibodies are detectable in urine that has not been diluted more than 250-fold, NY-ESO-1 antibodies were not detected in urine. Thus, these experiments demonstrate that NY-ESO-1 antibodies are present in the urine of patients who show high serum antibody titers (i.e., $\geq$1:1000). Also, the presence of the antibodies is not associated with reduced renal function, as the antibody was found in the urine of patients with normal renal function.

Example 4

Detection of NY-ESO-1 Serum and Urine Antibody

Both Western blot and ELISA assays have been standardized to detect NY-ESO-1 serum antibody. (Jager et al. (1999) *Int. J. Cancer* 84: 506–10; Stockert et al. (1998) *J. Exp. Med.* 187: 1349–54). In this study, NY-ESO-1 serum antibody reactivity was assessed by Western blot analysis, and the results were confirmed by ELISA in a subset of 10 serum samples. To exclude any non-specific reactivity with the recombinant NY-ESO-1 protein, sera were also tested against lysates of the NY-ESO-1-positive melanoma cell line NW-MEL-38.

Forty-three patients with advanced NY-ESO-1-positive malignancies (including melanoma 11, prostate cancer 5, breast cancer 4, stomach cancer 2, non-small cell lung cancer 9, ovarian cancer 3, sarcoma 3, cholangiocellular carcinoma 1, Non-Hodgkin's lymphoma 1, small cell carcinoma 2, multiple myeloma 1, bladder cancer 1) were selected for the assessment of NY-ESO-1 serum and urine antibody. Of the 43 patients tested, 17 had a strong NY-ESO-1 serum-antibody reactivity detectable at serum dilutions $\geq 1:1.000$. Seven patients had a weak antibody reactivity—faint bands at 1:250 dilutions and negative at 1:1.000 dilutions—and 19 patients had no detectable NY-ESO-1 serum antibody. Only those patients with high-titer ($\geq 1:1000$) serum antibody exhibit detectable urine antibody. In low-titer serum ($\leq 1:250$), even when NY-ESO-1 antibodies are detectable, antibodies were not detected in urine. Thus, these experiments demonstrate that NY-ESO-1 antibodies are present in the urine of patients who show strong titers of serum antibody (i.e., $\geq 1:1000$).

Example 5

Reactivity of Serum and Urine Antibody with Recombinant NY-ESO-1

Western blots were conducted using full-length recombinant NY-ESO-1 protein, recombinant SSX protein—used as a negative control—a lysate of NY-ESO-1-positive-tumor cells (NW-MEL-38) cultured in Dulbecco's modified Eagle's medium (10 mM HEPES buffer, L-arginine (84 mg/l), L-glutamine (584 mg/l), penicillin (10 IU/ml), streptomycin (100 ug/ml), and 10% FCS), and a lysate of COS-7 cells which had been transfected with cDNA encoding full-length NY-ESO-1. Serum and urine samples from NY-ESO-1-positive individuals contain antibodies that bind naturally-occurring NY-ESO-1 and COS-7 lysates containing recombinant NY-ESO-1. The serum and urine antibodies from these individuals did not bind SSX protein or cells that do not express NY-ESO-1.

Recombinant NY-ESO-1 was prepared in COS-7 cells and lysed to yield COS-7 lysates. The full-length coding sequence of NY-ESO-1 was cloned into BamHI-HindIII sites of the pcDNA3.1(−) vector, and this construct was used for the transfection of COS-7 cells. (Jager et al. (1998) *J. Exp. Med.* 187: 265–70). Lysates of NY-ESO-1-transformed COS-7 cells were applied to membranes and subsequently contacted with a urine sample from the lung cancer patient positive for antibodies to NY-ESO-1. Patient urine was tested in undiluted form, as well as after being diluted 1:100, and 1:1000. Negative controls were conducted using urine from an NY-ESO-1-negative individual, urine from an NY-ESO-1-positive individual diluted 1:2500, and without urine. Both undiluted and diluted (1:100) urine detect a 22 kDa protein that corresponds to the known molecular weight of the recombinant NY-ESO-1 protein. Detection of this 22 kDa protein indicates the presence of NY-ESO-1-specific antibodies in patient urine and demonstrates that recombinant NY-ESO-1 is a suitable agent for the detection of either serum or urine NY-ESO-1-specific antibodies.

Western blots of recombinant-NY-ESO-1 protein and lysates of NY-ESO-1-positive NW-MEL-38 cells—using serum and urine from the NY-ESO-1-positive, non-small-cell lung-cancer (NSCLC) patient NW900 and the NY-ESO-1-positive, melanoma patient NW29—demonstrate that both serum and urine antibodies bind recombinant and naturally-occurring NY-ESO-1 in Western blot assays.

Example 6

Identification of Tumor-specific Antigens Using SEREX and UREX Methods

A testicular cDNA expression library was screened using the SEREX method and serum isolated from breast cancer patient NW1189. Three tumor-associated antigens—NY-BR-1 (GenBank Accession Nos. XM165546 and XM166711 (both version 1 and submitted May 13, 2002); Cross et al. (2000) *Mamm. Genome* 11(5): 373–383; all incorporated herein by reference), SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference), and NW-BR-3 (GenBank Accession No. AJ236609 (May 2, 2000; version 1) and the UniGene designation Hs.339651; both incorporated herein by reference)—were identified. These three tumor-associated clones expressing the antigens NY-BR-1 (GenBank Accession Nos. XM165546 and XM166711 (both version 1 and submitted May 13, 2002); Cross et al. (2000) *Mamm. Genome* 11(5): 373–383; all incorporated herein by reference), SCP-1 (SEQ ID NO: 2; GenBank Accession No. D67035 (Feb. 2, 1999; version 1); Kondoh et al. (1997) *Cytogenet. Cell. Genet.* 78(2): 103–104; all incorporated herein by reference), and NW-BR-3 (GenBank Accession No. AJ236609 (May 2, 2000; version 1) and the UniGene designation Hs.33965 1; both incorporated herein by reference) were screened using urine isolated from breast cancer patient NW1189. The urine used in these screenings was undiluted and not preabsorbed. The three tumor-associated clones were positive and their identity was confirmed by sequencing.

Example 7

Comparison of Western Blot and UREX Analysis

The detection of NY-ESO-1-specific antibodies using NY-ESO-1 expressing clones, following the standard SEREX methodology but with the substitution of urine instead of serum, was compared to the detection of NY-ESO-1-specific antibodies using isolated NY-ESO-1. Undiluted urine antibody from patients NW29, NW1716, and NW1622 was used in each assay. Both assays produced to identical results.

Although the present invention has been described in detail with reference to the examples above, it is understood that various modifications can be made without departing from the spirit of the invention. All cited patents, patent applications and publications referred to in this application are herein incorporated by reference in their entirety.

We claim:

1. A method for determining that a patient suffers from a cancer characterized by aberrant expression of a cancer-testis (CT) antigen, consisting of:
   i) contacting a urine containing sample from a patient that is believed to suffer from said cancer with a cancer-testis (CT) antigen that specifically binds to an antibody present in said urine and characteristic of said cancer, under conditions favoring complex formation between the cancer-testis (CT) antigen and the antibody; and
   ii) detecting the complex between the cancer-testis (CT) antigen and the antibody present in said urine,
wherein presence of the antibody, as indicated by formation and detection of the complex indicates that the patient suffers from said cancer, wherein the cancer-testis (CT) antigen is NY-ESO-1 (SEQ ID NO:1), the protein encoded by the nucleic acid sequence of SEQ ID NO: 2 (SCP-1) or the protein encoded by the nucleic acid sequence of SEQ ID NO: 3 (clone 18CGI1F2).

2. The method of claim 1, wherein the cancer-testis (CT) antigen is NY-ESO-1.

3. A method for determining that a patient suffers from a cancer characterized by aberrant expression of a cancer-testis (CT) antigen, comprising:
   i) contacting a urine containing sample from a patient that is believed to suffer from said cancer with a cancer-testis (CT) antigen tat specifically binds to an antibody present in said urine and characteristic of said cancer, under conditions favoring complex formation between the cancer-testis (CT) antigen and the antibody; and
   ii) detecting the complex between the cancer-testis (CT) antigen and the antibody present in said urine,
wherein presence of the antibody, as indicated by formation and detection of the complex indicates that the patient suffers from said cancer, wherein the cancer-testis (CT) antigen is NY-ESO-1 (SEQ ID NO:1), the protein encoded by the nucleic acid sequence of SEQ ID NO: 2 (SCP-1) or the protein encoded by the nucleic acid sequence of SEQ ID NO: 3 (clone 18CGI1F2).

4. The method of claim 3, wherein the cancer-testis (CT) antigen is NY-ESO-1.

* * * * *